United States Patent
Lee et al.

(10) Patent No.: US 6,730,268 B2
(45) Date of Patent: *May 4, 2004

(54) DEVICE AND METHODS FOR SINGLE STEP COLLECTION AND ASSAYING OF BIOLOGICAL FLUIDS

(75) Inventors: Jin Po Lee, 13150 Glen Cir., Poway, CA (US) 92064; Poyi Tseng, Taipei (TW)

(73) Assignee: Jin Po Lee, Poway, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/366,921

(22) Filed: Feb. 13, 2003

(65) Prior Publication Data

US 2003/0129088 A1 Jul. 10, 2003

Related U.S. Application Data

(63) Continuation of application No. 09/509,378, filed as application No. PCT/US99/18881 on Aug. 18, 1999, now Pat. No. 6,548,019, which is a continuation-in-part of application No. 09/192,969, filed on Nov. 16, 1998, now Pat. No. 6,379,620.

(51) Int. Cl.[7] .............................................. G01N 21/00
(52) U.S. Cl. .......................... 422/58; 422/55; 422/56; 422/68.1; 422/57; 422/99; 422/102; 436/178; 436/180; 436/518
(58) Field of Search .................... 422/58, 56, 68.1, 422/57, 99, 102, 55; 436/518, 180, 178

(56) References Cited

U.S. PATENT DOCUMENTS

| | | | |
|---|---|---|---|
| 3,849,256 A | * 11/1974 | Linder | 435/287.7 |
| 4,943,522 A | 7/1990 | Eisinger et al. | |
| 5,252,496 A | 10/1993 | Kang et al. | |
| 5,384,264 A | 1/1995 | Chen et al. | |
| 5,403,551 A | * 4/1995 | Galloway et al. | 422/58 |
| 5,409,664 A | 4/1995 | Allen | |
| 5,523,055 A | * 6/1996 | Hansen et al. | 422/58 |
| 5,602,040 A | 2/1997 | May et al. | |
| 5,618,494 A | 4/1997 | Bunce et al. | |
| 5,656,502 A | 8/1997 | MacKay et al. | |
| 5,714,389 A | 2/1998 | Charlton et al. | |
| 5,770,458 A | * 6/1998 | Klimov et al. | 436/518 |
| 6,379,620 B1 | * 4/2002 | Tydings et al. | 422/58 |
| 6,497,843 B2 | * 12/2002 | Tydings | 422/58 |
| 6,548,019 B1 | * 4/2003 | Lee et al. | 422/58 |
| 6,616,893 B1 | * 9/2003 | Pham | 422/58 |
| 2002/0094301 A1 | * 7/2002 | Tydings et al. | 422/58 |
| 2003/0165405 A1 | * 9/2003 | Tydings | 422/58 |

FOREIGN PATENT DOCUMENTS

EP          0 333 286 A1    9/1989

* cited by examiner

Primary Examiner—Jill Warden
Assistant Examiner—Sam P. Siefke
(74) Attorney, Agent, or Firm—Stacy Taylor; Foley & Lardner

(57) ABSTRACT

Devices, and methods for the use of same, for collecting and assaying a biological fluid in a single step. One method provides means to control and direct the flow of a sample of the biological fluid directly onto an assay test strip by disposing the assay test strip within a flow control channel in which the internal ambient pressure is maintained in substantial equilibrium with the ambient pressure outside of the flow control channel, such that essentially no pressure gradient is formed within the flow control channel. The devices include the flow control channel, at least one assay test strip and a fluid sample collection container, such as a urine cup, for insertion of the flow control channel therein.

15 Claims, 2 Drawing Sheets

EXISTING DEVICE

EXISTING DEVICE

DEVICE AND METHODS FOR SINGLE STEP COLLECTION AND ASSAYING OF BIOLOGICAL FLUIDS

STATEMENT REGARDING RELATED APPLICATIONS

This application is a continuation application of U.S. patent application Ser. No. 09/509,378, filed on Mar. 23, 2000 now U.S. Pat. No. 6,548,019, currently pending; which is a 371 national phase entry of PCT/US99/18881, filed on Aug. 18, 1999; which is a continuation-in-part of co-owned U.S. patent application Ser. No. 09/192,969, filed on Nov. 16, 1998, now issued as U.S. Pat. No. 6,379,620.

BACKGROUND OF THE INVENTION

1. Field of the Invention

The invention relates to immunoassay devices and methods for collection and assaying of biological fluids, particularly urine. The invention further relates to means for controlling fluid flow through a wicking membrane.

2. History of the Related Art

With the increasing availability and use of drugs by the general population, employers such as government agencies, sports groups and transportation related companies utilize drug screenings as both conditions of employment and maintenance of safety in the workplace. To have a doctor present at the workplace to perform the drug screenings is both expensive and impractical for an employer. Accordingly, other methods have been developed to perform the drug screenings.

One such method is exemplified in U.S. Pat. No. 5,403,551 entitled "Assaying Device and Container for In Field Analysis of a Specimen and Later Shipment of the Unadulterated Specimen." This device is relatively expensive to manufacture because it requires specialized components (particularly a special fluid collection cup), and is relatively complex to operate by laymen, as well as being subject to leakage and contamination.

SUMMARY OF THE INVENTION

The invention provides means for controlling assay sample fluid flow through an assay test strip for use in performing immunoassays in a dipstick format. In particular, fluid flow control is accomplished by placing the assay test strip within a flow control channel in which the ambient pressure within the flow control channel is maintained in substantial equilibrium with the ambient pressure outside the flow control channel.

By avoiding the formation of a pressure gradient within the flow control channel along which assay sample fluid would be encouraged to flow into the flow control channel, fluid flow from the sample source into which the dipstick assay test strip is immersed is substantially limited to migration by wicking through the test strip. In this fashion, the risk of oversaturation of the test strip on introduction into an assay sample fluid is minimized. As such, the need for other means of restricting the rate or volume of flow through a dipstick assay test strip, such as a housing with a limited volume sample application port or steps to indirectly introduce sample onto the test strip, is also avoided, thereby reducing manufacturing costs and increasing the speed of assay performance.

The invention further provides a combination assaying device and collection chamber which is capable of easily collecting and testing a biological fluid sample, such as urine, while maintaining the sample unadulterated and secure. In particular, the invention provides a fluid flow control test strip in a chamber on a solid support introduced into a fluid collection chamber, such as a urine cup, wherein the volume capacity of the assay sample fluid collection container is such that the total fluid pressure obtainable within the container is maintained at or below 1 atmosphere.

BRIEF DESCRIPTION OF THE DRAWINGS

The above-mentioned features and objects of the present invention will become more apparent with reference to the following description taken in conjunction with the accompanying drawings wherein like reference numerals denote like elements and in which.

DETAILED DESCRIPTION OF TILE INVENTION

Definitions

Figure 1:
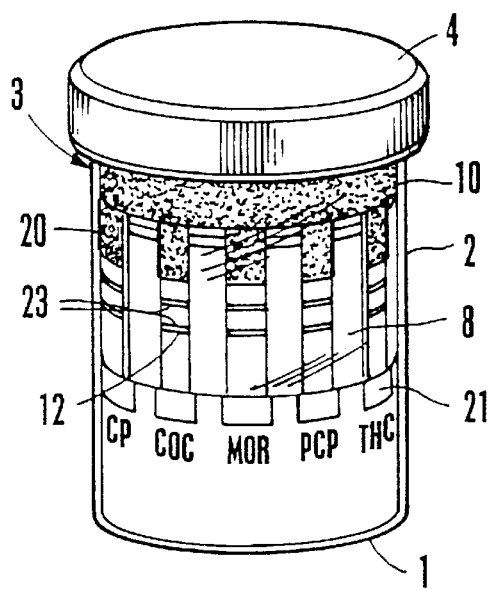
FIG. 1 is a side view of a combination collection cup/dipstick assay means device which is improved upon by the invention.

For ease of understanding, the following definitions will apply throughout this description; however, no definition should be regarded as being superceding any art-accepted understanding of the listed terms.

The term "analyte" as used herein refers to any substance which is capable of binding either antibodies or antigens. Antigens may comprise, without limitation, chemical compounds, polypeptides, carbohydrates, nucleic acids, lipids, and the like, including viral particles, viral subunits, bacterial and parasite surface antigens, and host proteins that may be diagnostic of the subject's condition.

A "test zone" refers to an area in which a binder (ligand) or analyte is attached, movably or immovably, to the assay test strip portion of an assay device.

A "sample loading zone" refers to an area of an assay test strip on which a fluid analyte sample is applied for migration to the test zone.

An "assay test strip" of the invention consists of, collectively, test and sample loading zone supporting membranes, as well as any filters present in the dipstick assay means of the invention.

An "assay sample fluid" can be any fluid suspected of containing analyte of interest for which a particular assay is specific. Test sample may represent any body fluid, including urine, blood, sweat, lymph, intraperitoneal fluid, crude tissue extract or homogenate, derived from a fetus, neonate, juvenile or adult subject; a non-biological fluid such as water from some ecological niche, e.g., a river or a lake; or a solution used in a laboratory.

A "label" is a molecule or compound which directly or indirectly mediates the formation of a signal (such as a color change) which is used in assay to indicate the presence, absence or concentration range of analyte of interest in a test sample. Labels may include enzymes, fluorescers, liposomes, erythrocyte ghosts, polymer microcapsules, color polymer particles (latex), and preferably includes sols of metal-containing compounds. A wide variety of patents and patent applications provide an extensive literature of different techniques for producing detectable signals in immunoassays. The following list of United States patents is merely illustrative of the type of label which can find application in this invention: U.S. Pat. Nos. 3,646,346 discloses radioactive label; 3,654,090, 3,791,932, and 3,817,838 disclose enzyme labels; U.S. Pat. No. 3,996,345 discloses fluorescer-quencher labels; U.S. Pat. No. 4,062,733 discloses radioactive label; U.S. Pat. No. 4,067,959 discloses fluorescer or enzyme label; U.S. Pat. No. 4,104,099 discloses chemiluminescent label; and U.S. Pat. No. 4,160,645 discloses non-enzymatic catalyst label. U.S. Pat. No. 3,966,879 discloses an electrophoretic technique employing an antibody zone and U.S. Pat. No. 4,120,945 discloses a radioimmunoassay (RIA) where labeled analyte is initially bound to a solid support through antibody. U.S. Pat. No. 4,233,402 discloses enzyme pair labels; U.S. Pat. No. 4,720,450 discloses chemically induced fluorescent labels; and U.S. Pat. No. 4,287,300 discloses enzyme anionic charge labels.

Labels can also be metal-containing sols; i.e., metal or metal compounds such as metal oxides, metal hydroxides, metal salts, metals or metal-containing compounds mixed with polymers or coated onto polymer nuclei. These metal labels may include dry forms of any of the above-named metal or metal compound sols, and preferably includes colloidal gold in dry form.

"Fluid communication" refers to structures which are in contact with, but not necessarily affixed to, one another.

"Assay" refers to several different types of assay formats in which an analyte of interest can be detected using an assay test strip. For example, in a sandwich-type immunoassay, analytes of interest in the analyte sample, when present, bind a labeled tracer movably incorporated in the assay test strip (consisting of a porous membrane) at the tracer zone to form a first complex. The tracer is a molecule which binds the analyte of interest and is conjugated to a label, preferably a metal label, and most preferably colloidal gold.

A second immobilized ligand corresponding to the analyte of interest is coupled to the assay test strip at the test zone. First complex and unbound labeled ligand mix with the test sample and be carried along therewith by capillary action (wicking) through the test zone. Analyte sample passes through the assay test strip bringing the first complexes, if any, into contact with the unlabeled ligand immobilized in the test zone to form a second complex of labeled ligand-analyte-immobilized ligand. The first immobilized ligand is immobilized in the test zone by means known in the art, including covalent bonding or attachment to an insoluble protein-coated surface (see, e.g., U.S. Pat. Nos. 4,200,690 and 5,075,078). When the second complex is formed, a visible color pattern appears in the test zone. Labeled ligand not bound to analyte in the test sample continue migration by wicking into the control zone to contact the ligand immobilized there. The labeled ligand can bind the immobilized ligand in the control zone to form a third complex, and thus be captured in the control zone.

The term "sample integrity monitoring system" refers to one or more strips on which a determinant indicative of conditions in a fluid sample are provided.

Representative Assay Device For Use With the Improvements of the Invention

Figure 2:
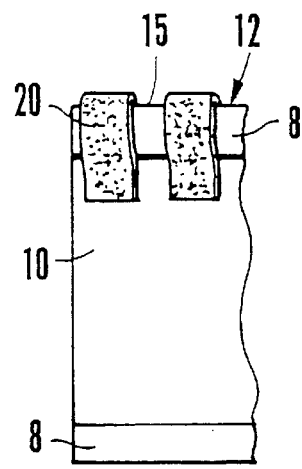
FIG. 2 is a cut-away view of the dipstick assay means of FIG. 1.

FIGS. 1 and 2 illustrate features of a combination dipstick assay test strip and urine collection cup device depicted in FIGS. 1 and 2, which device may be improved by application of the features of the invention. In this device, one or more assay test strips 12 are provided on one side of a two-sided solid support backing 8. Assay test strip 12 is conventional in design, and includes sample loading zone 20 in fluid communication with a test zone 23 into which are incorporated labels and reagents indicative of the presence or absence of analyte in the assay sample fluid. A printed tag 21 indicative of the identity of the material for which the assay is specific may optionally be included on test strip 12 distal to sample loading zone 20.

The opposite side of backing 8 is covered with wicking material 10. Wicking material 10 is brought into contact with assay test strip 12 by either being folded at one end over test strip 12 (FIG. 1), or by being covered at one end by assay test strip 12 (FIG. 2). In the latter embodiment, sample loading zone 20 of assay test strip 12 is folded over top edge 15 of backing 8 and layered onto wicking material 10.

Referring to FIG. 1, backing 8 is shaped to fit within and follow the inner diameter of a transparent urine collection cup 2, having mouth 3 and base 1. In use, backing 8 is inserted into cup 2 so sample loading zone 20 of dipstick 12 is flush with mouth 3 of cup 2. Urine is collected into cup 2, then the fluid wicks up wicking material 10 to contact sample loading zone 20 of assay test-strip 12. Cup 2 may then be sealed with cap 4. Eventually, the fluid migrates through assay test strip 12 to contact the assay reagents incorporated therein. Results of the assay are viewed through the transparent sides of the urine cup.

Although an improvement over prior art assay devices, the representative device of FIGS. 1 and 2 has several limitations. First, it is relatively slow to produce results in comparison to other devices due to the time necessary for assay sample fluid to wick up wicking material 10 toward assay test strip 12 (in many other dipstick assay devices, assay sample fluid is applied directly on, or adjacent to, a sample loading zone).

Second, assay sample fluid may not wick evenly through wicking material 10 if a minimum volume of assay sample fluid is not introduced into cup 2, or if so much assay sample fluid is introduced that wicking material 10 becomes flooded. Consequently, where the assay device includes multiple assay test strips, different volumes of fluid may be loaded onto each test strip. At times, this limitation has resulted in the failure of the device to produce reliable assay results on one or more of the test strips.

Third, the need to overlap wicking material 10 and sample loading material 20 increases the number of steps, and therefore the cost, necessary for manufacture of the device.

Theoretically, the use of wicking material 10 as a vehicle to deliver assay sample fluid to assay test strip 12 could be eliminated by simply reversing the orientation of sample loading zone 20 in cup 2 so it is adjacent with base 1, rather than mouth 3, retaining all other features of the device. In such an orientation, sample loading zone 20 would come into direct contact with assay sample fluid introduced into cup 2. In practice, however, this alternative fails because test subjects usually provide such quantities of assay sample fluid into urine collection cups that assay test strip 12 rapidly becomes flooded.

These enumerated limitations of the assay device of FIGS. 1 and 2 are overcome by the present invention. In particular, the invention provides an assay device in which assay fluid sample is introduced directly to the sample loading zone of an assay test strip, wherein the device further includes means to control and direct assay sample fluid flow into the test strip, thereby avoiding oversaturation of the test strip, even in the presence of a substantial volume of assay sample fluid. Where more than one test strip is present in the device of the invention, assay sample fluid is introduced evenly into each strip, even in the presence of very small or very large volumes of assay sample fluid. Advantageously, the invention is relatively simple to manufacture.

Assay Devices of the Invention

For ease of understanding, the various embodiments of the invention will be described by reference to their application in a combination assay test strip/assay sample fluid collection cup. However, those of ordinary skill in the art will appreciate that the flow control means of the invention common to each embodiment may be utilized in any test-strip based immunoassay format in which restricting the flow of fluid through the test strip is desired.

Figure 3:
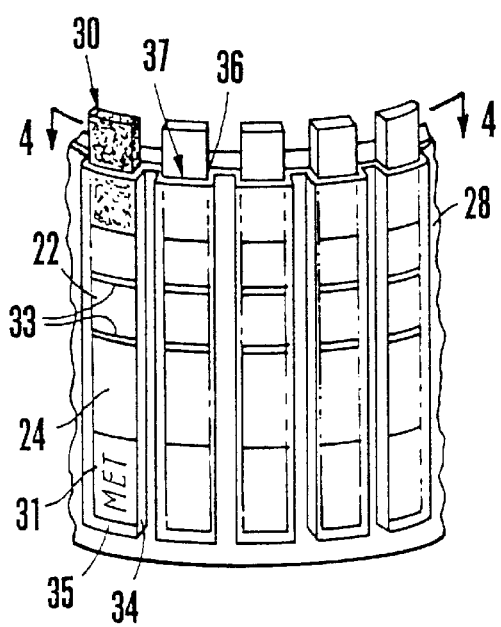
FIG. 3 is a front view of a flow control dipstick assay means of the invention.

Turning to FIG. 3, an example of the flow control means of the invention is depicted. The dipstick assay device component of the invention 40 consists of assay test strip 22 and a support therefor (backing 28, described below). In the FIGURE, assay test strip 22 is disposed on one side of a two-sided backing 28. Backing 28 which is made from a resilient, liquid impermeable material. Typically one such material would be a plastic or plastic coated sheet which is not reactive with any of the components of the biological fluid to be assayed; e.g., urine.

Assay test strip 22 is conventional in design. Therefore, because those of ordinary skill in the art will be abundantly familiar with the design of such assay test strips, they will not be described in detail here. Briefly, assay test strip 22 comprises bibulous membrane 24, and includes sample loading zone 30 in fluid communication with a test zone 33 into which labels and reagents are incorporated, which labels and reagents are capable of providing an observable signal indicative of the presence or absence of analyte in an assay sample fluid. Optionally, printed tag 31 identifying the material for which the assay is specific is included on test strip 22 distal to sample loading zone 30.

For further review concerning assay test strip construction, including selection and preparation of test reagents, the following references provide a representative sample of assay test strip designs known in the art: U.S. Pat. No. 5,384,264 (commonly owned); U.S. Pat. No. 4,491,645; U.S. Pat. No. 4,943,522; U.S. Pat. No. 5,252,496; U.S. Pat. No. 5,714,389 and U.S. Pat. No. 5,602,040, the disclosures of which are incorporated for purposes of reference.

As shown in FIG. 3, backing 28 is shaped to fit within and follow the inner diameter of a transparent urine collection cup 2 (FIGS. 6 and 7), having mouth 3 and base 1. In one embodiment of the invention, backing 8 is inserted into cup 2 so sample loading zone 30 of assay test strip 22 is disposed near base 1 of cup 2.

Assay sample fluid control in this embodiment of the invention is accomplished by disposing assay test strip 22 within a flow control channel, wherein the ambient pressure within the flow control channel is maintained in substantial equilibrium with the ambient pressure outside of the flow control channel even after placement of the flow control channel into collection container which contains assay sample fluid. The dimensions of the assay sample fluid collection container of the invention are such that the total volume of sample fluid into which the flow control channel is placed is maintained below the depth at which equilibrium in ambient pressure within and without the flow control channel would be lost.

In general principle, an assay sample fluid depth in a column of approximately 10 meters would be required to produce an ambient pressure of substantially more than 1 atmosphere. For most biological fluid assay applications of the inventive flow control means, the total volume of assay sample fluid to be utilized will be well below what would be required to produce such a depth.

The flow control channel of the invention will be formed of five liquid impervious, and one liquid pervious, sides. For example, as shown, collectively, in FIGS. 3 and 4, flow control channel 34 has five liquid impervious walls 35, 35A, 35B, 35C and backing 28, and one liquid pervious side consisting of an opening 36 through which sample loading zone 30 of assay test strip 22 protrudes. In total size, both flow control channel 34 and backing 28 are necessarily smaller than any assay sample fluid collection container into which they are to be placed.

As a further example, the liquid pervious side of the flow control channel may also be formed as an orifice in a liquid impervious side, or the liquid pervious side may consist of a liquid permeable membrane. The liquid pervious side of the flow control channel is necessary to allow the pressure within and without the flow control channel to maintain substantial equilibrium notwithstanding immersion into sample fluid and entry of fluid into the assay test strip disposed within the flow control channel.

By maintaining substantial ambient pressure equilibrium about the flow control channel, no pressure gradient is allowed to form along which fluid outside the flow control channel will flow into the flow control channel. As such, fluid entry into the flow control channel is limited to migration into assay test strip 22; e.g., by wicking fluid from sample loading zone 30 toward and through test zone 33.

Figure 4:
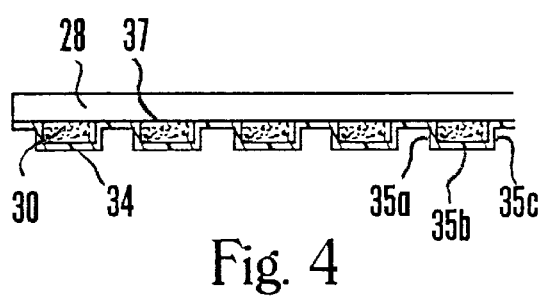
FIG. 4 is a cross-section of FIG. 3 along line 4—4 of FIG. 3.

To this end, flow control channel 34 is preferably disposed over assay test strip 22 (FIG. 4). Flow control channel 34 has two opposing ends; liquid impervious closed end side 35 and liquid pervious open end 36. Open end 36 has an opening 37 which is loosely fitted around test strip 22, whose sample loading zone 30 protrudes beyond opening 37. In use, the test subject introduces an assay sample fluid (typically urine) into a fluid sample container, such as cup 2, through mouth 3. Closed end 35 of flow control channel 34 blocks sample fluid from entering the flow control channel as it is introduced through mouth 3.

As shown in FIG. 3, separate flow control channels are provided for each of multiple assay test strips. However, in view of the foregoing teaching concerning the mole of ambient pressure equilibrium in flow rate control, those of ordinary skill in the art will appreciate that flow restriction could also be provided by alternative flow control channel designs; e.g., flow control channel 34 may be continuous in width so all test strips are disposed within the same air pocket defined by the flow control channel.

As assay sample fluid collects in cup 2, it contacts sample loading zone 30 and begins migrating upwards through assay test strip 22. So long as the volume of fluid introduced into cup 2 is sufficient to contact sample loading zone 30 (which may itself be placed into contact with base 1 of cup 2 to minimize the necessary volume of assay sample fluid), any amount of assay fluid up to the maximum volume capacity of cup 2 may be used in performing an assay with the device of the invention. In devices with multiple assay test strip, the sample loading zone of each is contacted by an equivalent volume of sample assay, thereby avoiding unequal distribution of sample assay fluid among the test strips.

Preferably, test zone 33 will be situated on test strip 22 at least 2 millimeters away from the distalmost end of sample loading zone 30 to isolate test zone 33 from fluid collecting around open end 36 of chamber 34. Assay test results are viewed through the transparent walls of cup 2. To ensure privacy of test results, the outside of cup 2 through which results are viewed may be covered, for example, with a piece of removable opaque tape. The assay sample fluid may be discarded after performance of the assay, and the dipstick assay device preserved, within or without cup 2.

Figure 5:
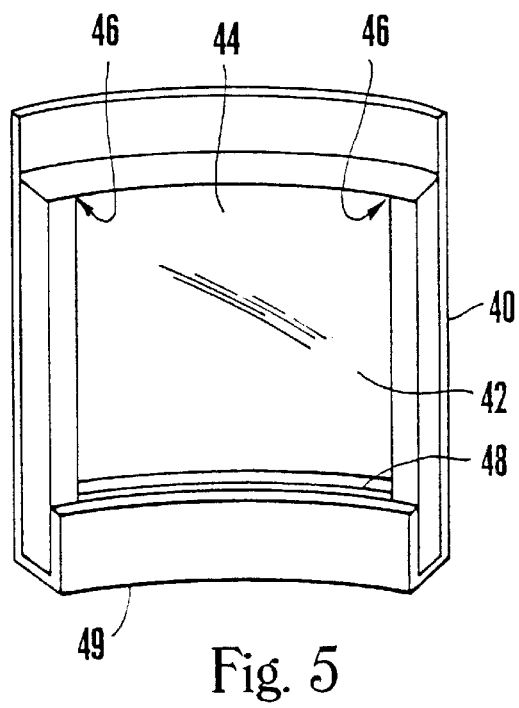
FIG. 5 is a front view of a holder for the dipstick assay means of FIGS. 3 and 4.
Figure 6:
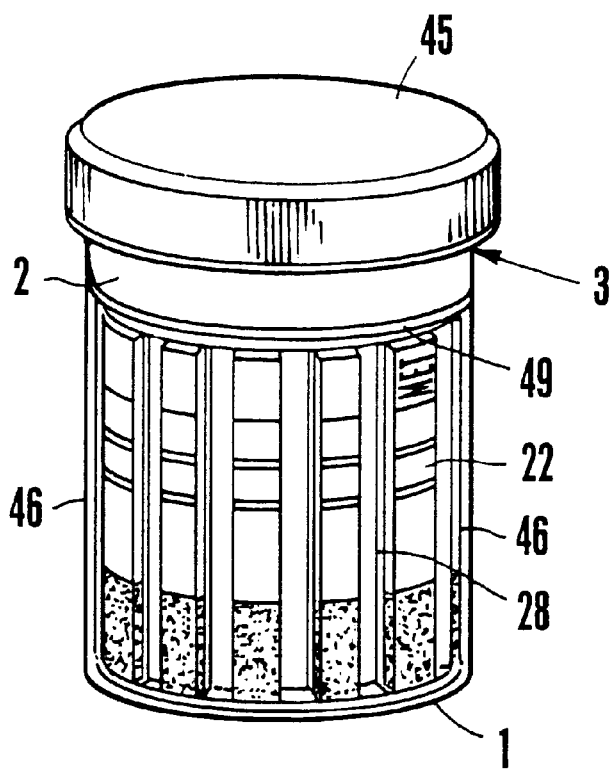
FIG. 6 is a front view of an assay sample fluid collection device of the invention, into which is inserted the dipstick assay means of FIGS. 3 and 4, as well as the holder of FIG. 5.

An optional addition to the invention is a holder for holding the assay device in place in cup 2 (FIG. 5). As shown in FIG. 5, the holder 40 is curved to follow the inner diameter of cup 2 and is substantially the same height as cup 2, although it will be appreciated that the holder may be of any configuration which will fit within cup 2 and hold backing 28 as described herein. Holder 40 includes curved portion 42 with a cut-out 44, defining vertical slots 46 and optional horizontal slot 48 for insertion of backing 28 therein. Curved portion 42 is shown in FIG. 4 as having end 49, which is optionally closed to protect backing 8 and may be beveled for ease of insertion of holder 40 into cup 2. In use, backing 28 is inserted into vertical slots 46 and horizontal slot 48 so, on insertion of holder 40 into cup 2, sample loading zone 30 of assay test strip 22 is oriented toward cup base 1 and end 49 of holder 40 is oriented toward cup mouth 3 (FIG. 6). The operation of this further embodiment of the invention proceeds as described above.

Figure 7:
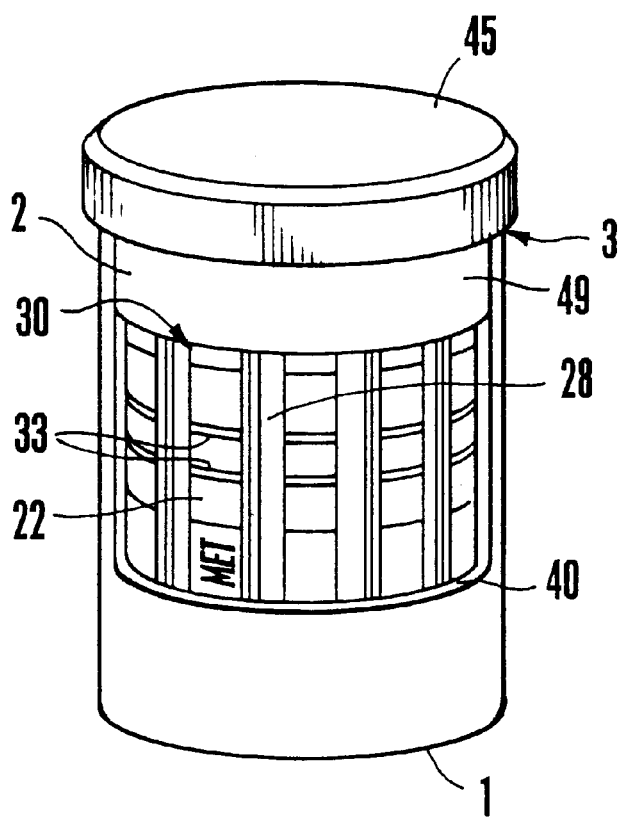
FIG. 7 is a front view of a further embodiment of an assay sample fluid collection device of the invention in combination with the dipstick assay means of FIGS. 3 and 4, as well as the holder of FIG. 5.

In an alternative embodiment of the invention (shown in FIG. 7), backing 28 is placed into holder 40 so sample loading zone 30 is inserted into horizontal slot 48. In this embodiment, horizontal slot 48 of cut-out 44 (FIG. 5) includes end 49 (including the optional closure of end 49, thereby defining a narrow liquid reservoir in the liquid pervious side of flow control channel 34 is enclosed. Holder 40 is placed into cup 2 so closed end 49, and sample loading zone 30 enclosed therein, are adjacent to mouth 3 of cup 2 (FIG. 7). Cap 45 (which may be of any design which provides a watertight seal; e.g., a screw-on or snap-fit design) is included to close cup 2.

The use of this embodiment of the invention proceeds as follows. Assay sample fluid (usually urine) is introduced into cup 2. When fluid collection is complete, cap 45 is placed onto cup 2 to provide it with a watertight seal. To perform the assay, the laboratory technician inverts cup 2 so assay sample fluid flows into horizontal slot 48. In this fashion, the combination of horizontal slot 48, vertical slots 46 and closed end 49 define a fluid reservoir into which sample loading zone 30 of assay test strip 22 becomes immersed on inversion of cup 2 (FIG. 8). Assay sample fluid then migrates evenly through assay test strip 22 and any other test strips present in the device. Assay results are viewed through the transparent walls of cup 2.

All of the foregoing embodiments of the invention share the advantage of providing for direct application of sample fluid to the assay test strip (as opposed to having the fluid migrate through an intermediate structure, such as wicking material 10 of FIGS. 1 and 2). As such, interassay variation derived from differential volume application to multiple test strips is avoided, and the entire assay may be performed more quickly than previously possible, at a lower manufacturing cost.

Although the invention may be utilized to assay any fluid for any analyte of interest, it is especially well adapted to screening urine for the presence of narcotics. To this end, a five drug panel of assay tests is recommended by the National Institute on Drug Abuse (NIDA), which includes tests for tetrahydrocannabinol and other marijuana metabolites, cocaine metabolites, opiate metabolites, phencyclidine (PCP, Angel Dust), and amphetamines. For a more extensive substance abuse testing panel, the choice of analytes tested can include marijuana metabolites; tetrahydrocannabinol and other marijuana metabolites, cocaine metabolites, opiate metabolites, phericyclidine (PCP, Angel Dust), amphetamines, barbiturates, benzodiazepines, methaqualone, and propoxyphene. The assay test strips for drug tests preferably have the sensitivity equal to the cutoffs recommended by Substance Abuse Mental Health Service Administration (SAMSHA) and NIDA, which most employers use. Binders and reagents for use in constructing assay test strips for use in detecting drugs of abuse are well known in the art and will not be described in detail here.

Subjects undergoing drug tests are sometimes creative in their efforts to adulterate the analyte samples to evade detection of drugs of abuse likely to be present in the sample. To minimize the effects of such evasion efforts on results obtainable with the assay devices of the invention, a sample integrity monitoring system will be incorporated into the device. Such a system is used to determine whether adulterants have been added to the sample or if its quality is otherwise compromised.

For example, the sample integrity monitoring system may evaluate any or all of the pH, osmolality (the total concentration of solutes in urine, expressed as mOsm/kg and measured as a function of fluid specific gravity) of, or albumin, creatinine, glutaraldehye and nitrite levels in, the sample. In the devices of the invention, the system is comprised of one or more additional test strips (not shown) placed on backing 28, or test path integrated into assay test strip 22 adjacent to printed tag 31 (as described in co-pending, commonly owned U.S. patent application Ser. No. 09/364,277, filed Jul. 29, 1999, now issued as U.S. Pat. No. 6,514,769).

It should be apparent to those skilled in the art that the above-described embodiments are merely illustrative of but a few of the embodiments which could be created by one of ordinary skill in the art without departing from the spirit and scope of the present invention.

The disclosure of all publications cited above are expressly incorporated herein by reference, each in its entirety, to the same extent as if each were incorporated by reference individually.

That which is claimed is:

1. A device for collecting and assaying a sample of biological fluid, the device comprising:

(a) a flow control channel defined by at least one liquid pervious side joined to liquid impervious sides, wherein the internal dimensions of the flow control channel are sufficient to permit placement therein of an assay test strip;

(b) an assay test strip within the flow control channel, wherein the assay test strip has a sample loading zone therein, and wherein further the assay test strip is disposed within the flow control channel so the sample fluid contacts the sample loading zone at a liquid pervious side of the flow control channel; and, (c) a sample fluid container having a base, an open mouth, and walls connecting the base to the mouth;

wherein the flow control channel is disposed inside the sample fluid container with the liquid pervious side oriented toward the mouth of the sample fluid container so that the assay sample fluid, when added to the container and then inverted, is delivered to the sample loading zone of the assay test strip by entry through a liquid pervious side of the flow control channel without migration through an intermediate structure, and wherein entry of fluid into the flow control channel creates an ambient pressure within the flow control channel equivalent to the ambient pressure outside of the flow control channel, thereby eliminating a pressure gradient along which excess sample fluid could flow into the flow control channel.

2. A device according to claim 1, wherein the sides of the flow control channel are loosely fitted around the assay test strip.

3. A device according to claim 1, wherein one of the liquid impervious sides of the flow control channel is formed as a portion of a liquid impervious backing; and wherein the device further comprises a holder fittable inside the fluid sample container, the holder having at least one slot formed therein to receive the backing.

4. A device according to claim 3, wherein both the holder and the fluid sample container are curved in shape, and the curvature of the holder follows the curvature of the inner diameter of the fluid sample container.

5. A device according to claim 4, wherein the fluid sample container is a cup.

6. A device according to claim 1, further comprising a watertight cap fittable over the mouth of the cup.

7. A device according to claim 3, wherein the slot formed in the holder is closed on five sides to define a liquid reservoir.

8. A device according to claim 7, wherein the backing is inserted into the holder such that a liquid pervious side of the flow control channel is enclosed in the slot of the holder.

9. A device according to claim 1, further comprising additional assay test strips, wherein the additional assay test strips detect the presence or absence of different analytes in a biological fluid.

10. A device according to claim 9, wherein all of the assay test strips are disposed in a single flow control channel.

11. A device according to claim 9, further comprising additional flow control channels, wherein each assay test strip is disposed in a separate flow control channel.

12. A device according to claim 9, wherein the different analytes are different narcotics.

13. A device according to claim 12, further comprising a sample integrity monitoring system, the system comprising one or more assay test strips into which reagents and labels are incorporated to provide a visually observable signal indicative of the presence of adulterants or contaminants in the biological fluid.

14. A device according to claim 9, wherein the biological fluid is urine.

15. A device according to claim 13, wherein the biological fluid is urine.

* * * * *